United States Patent
Maarschalk et al.

(10) Patent No.: US 10,660,869 B2
(45) Date of Patent: May 26, 2020

(54) LACTATE POWDER AND METHOD FOR THE PREPARATION THEREOF

(71) Applicant: Purac Biochem B.V., Gorinchem (NL)

(72) Inventors: Kees Van Der Voort Maarschalk, Wijchen (NL); Heny Kusumawardani, Papendrecht (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

(21) Appl. No.: 14/418,865

(22) PCT Filed: Jul. 31, 2013

(86) PCT No.: PCT/NL2013/050572
§ 371 (c)(1),
(2) Date: Jan. 30, 2015

(87) PCT Pub. No.: WO2014/021718
PCT Pub. Date: Feb. 6, 2014

(65) Prior Publication Data
US 2015/0150835 A1 Jun. 4, 2015

Related U.S. Application Data

(60) Provisional application No. 61/678,139, filed on Aug. 1, 2012.

(30) Foreign Application Priority Data

Aug. 1, 2012 (EP) ..................................... 12178808

(51) Int. Cl.
*A61K 31/19* (2006.01)
*A23L 2/52* (2006.01)
*A61K 31/70* (2006.01)
*A61K 33/06* (2006.01)
*A23L 33/16* (2016.01)
*A61K 9/16* (2006.01)

(52) U.S. Cl.
CPC ................ *A61K 31/19* (2013.01); *A23L 2/52* (2013.01); *A23L 33/16* (2016.08); *A61K 9/16* (2013.01); *A61K 9/1694* (2013.01); *A61K 31/70* (2013.01); *A61K 33/06* (2013.01); *A23V 2002/00* (2013.01)

(58) Field of Classification Search
None
See application file for complete search history.

(56) References Cited

U.S. PATENT DOCUMENTS

| 2,143,361 | A |  | 1/1939 | Morgan et al. |  |
|---|---|---|---|---|---|
| 2,222,520 | A | * | 11/1940 | Sturm | A61K 33/06 514/557 |
| 2,856,326 | A | * | 10/1958 | Shaw | A61K 33/06 514/557 |
| 4,501,758 | A | * | 2/1985 | Morris | A23L 25/25 426/103 |
| 5,274,152 | A | * | 12/1993 | Carmody | A61K 8/26 424/68 |
| 5,716,811 | A |  | 2/1998 | Nauth |  |
| 7,494,684 | B2 | * | 2/2009 | Cruz | C07C 51/412 426/652 |
| 2005/0287272 | A1 |  | 12/2005 | Zheng et al. |  |
| 2008/0125488 | A1 | * | 5/2008 | Leverve | A61K 31/19 514/557 |
| 2008/0152764 | A1 |  | 6/2008 | Kremer et al. |  |
| 2010/0062503 | A1 | * | 3/2010 | Visser | C13B 10/08 435/135 |
| 2011/0300220 | A1 |  | 12/2011 | Coszach et al. |  |

FOREIGN PATENT DOCUMENTS

| EP | 1 797 773 A1 | 6/2007 |  |
|---|---|---|---|
| JP | 63-225332 | 9/1988 |  |
| JP | 2502572 B2 * | 5/1996 | ............ A61K 8/365 |
| WO | WO-00/28973 A1 | 5/2000 |  |
| WO | WO 03031385 A1 * | 4/2003 | .......... C07C 51/412 |
| WO | WO 2010/111680 A2 | 9/2010 |  |
| WO | WO 2012/030664 A1 | 3/2012 |  |

OTHER PUBLICATIONS

PURASAL® Powder S 100 specification sheet 2016 (Year: 2016).*
International Search Report for Application No. PCT/NL2013/050572 dated Sep. 23, 2013.
"Purasal P HiPure 60 Specification", Internet Citation, Sep. 19, 2002, XP002213995, retrieved from the Internet: URL:http://www.purac.com/products/EN-PHiPure60NPL.pdf, 1 page.
De Vuyst, et al., "Nisin, A lantibiotic produced by *Lactococcus lactis* subsp. lactis: properties, biosynthesis, fermentation and applications" In: De Vuyst, L. et al: Bacteriocins of lactic acid bacteria, Chapman Hall (1994) Chapter 5, pp. 151-221.
Kalra, et al., "Effect of calcium carbonate on nisin production in a milk culture", Indian Journal of Dairy Science, (1973) vol. 261-15, pp. 146-148.

(Continued)

*Primary Examiner* — Robert A Wax
*Assistant Examiner* — Caralynne E Helm
(74) *Attorney, Agent, or Firm* — Gilberto M. Villacorta; Sunit Talapatra; Foley & Lardner LLP

(57) ABSTRACT

The present invention relates to a lactate powder, more particularly a lactate powder having a lactate content of at least 20 wt. % and a water content of less than 3.5 wt. %, said powder comprising calcium cations as well as sodium cations. According to the invention, a calcium lactate powder combining high stability with excellent water dissolution properties can be obtained even though anhydrous calcium lactate represents the bulk of the powder if the powder additionally contains a certain amount of sodium lactate. The inventors have found that the presence of sodium lactate greatly improves the dissolution behavior of the anhydrous calcium lactate while maintaining the storage stability of the powder. The present inventors also established that the dissolution behavior of the powder can be further improved by the addition of a fast-dissolving carbohydrate material.

13 Claims, No Drawings

(56) References Cited

OTHER PUBLICATIONS

Perez-Guerra, N. et al., "Production of bacteriocins from *Lactococcuslactis* subsp. lactis CECT 539 and pediococcus acidilactici NRRL B-5627 using mussel-processing wastes", Biotechnology and Applied Biochemistry (2002) vol. 36, No. 2, pp. 119-125.

Van'T Hul, et al., "Neutralization/recovery of lactic acid from Lactococcus lactis: effects on biomass, lactic acid, and nisin production", World Journal of Microbiology and Biotechnology (1997) vol. 13, No. 5, pp. 527-532.

\* cited by examiner

LACTATE POWDER AND METHOD FOR THE PREPARATION THEREOF

This Application is the National Phase of International Patent Application No. PCT/NL2013/050572 filed Jul. 31, 2013, published as WO 2014/021718, which claims priority to European Patent Application No. 12178808.7 filed Aug. 1, 2012 and U.S. Provisional Application No. 61/678,139, filed Aug. 1, 2012. The contents of this application is herein incorporated by reference in its entirety.

TECHNICAL FIELD OF THE INVENTION

The present invention relates to a lactate powder, more particularly a lactate powder having a lactate content of at least 20 wt. % and a water content of less than 3.5 wt. %, said powder comprising calcium cations as well as sodium cations.

The invention also provides a method of preparing such a lactate powder by means of spray drying.

BACKGROUND OF THE INVENTION

Calcium lactate is a white crystalline salt with chemical formula $[CH_3CH(OH)COO]_2Ca$. Calcium lactate exists in various forms: anhydrous amorphous material, crystalline pentahydrate and mixtures thereof.

Calcium lactate is used in calcium fortification of juices and juice drinks, nectars, non-clear beverages, acidified dairy/soy drinks, powdered drinks, infant food and is formulated into capsules, tablets and liquids as therapeutic or nutritional supplement. Furthermore, calcium lactate is used as a food preservative.

The calcium lactate products that are commercially available are generally obtained by mass crystallisation followed by grinding or by spray drying. The calcium lactate powders so obtained typically contain high levels of calcium lactate pentahydrate. Calcium lactate in the crystalline pentahydrate form has favourable dispersion properties so that it can very easily be dissolved in water. However, in mixtures containing calcium lactate, presence of water of hydration is also a disadvantage because the water can be extracted from the crystal by other components that are hygroscopic in nature. Take-up of moisture originating from calcium lactate pentahydrate by such hygroscopic components, can result in the entire product becoming sticky. Clearly, this negatively affects the properties of the product. To prevent water uptake of the hygroscopic component, calcium lactate should be used in the anhydrous form.

Anhydrous calcium lactate, on the other hand, is notoriously difficult to dissolve in water. When particles of anhydrous calcium lactate come into contact with water these tend to form lumps that dissolve very slowly.

An example of a commercially available calcium lactate pentahydrate powder is PURACAL® PP/FCC (marketed by Purac, now Corbion). This product contains 13.4-14.5% (w/w) calcium and exhibits a loss on drying of 22.0-27.0% (w/w). This particulate material (surface-based average particle size, D[32], of 184 µm) has a solubility in water of 9 g/100 ml at 25° C. The typical dissolution time of this powder is 25 seconds (when 1000 mg of a sample is dissolved in 240 ml water).

US 2011/300220 describes solid calcium lactate in the form of substantially spherical particles, said spherical particles having a particle size distribution such that most of the particles are between 280 and 550 microns in size and the calcium lactate can be rapidly dissolved in water. This US patent application describes a method for the production of these spherical calcium lactate particles, comprising:

in a first step, a calcium lactate solution is atomised in a fluidised bed granulator at an incoming air temperature of less than 80° C.;

the wet substantially spherical calcium lactate particles are retrieved; and in a second step, said wet particles undergo a heat treatment in a fluidised bed at an incoming air temperature of less than 165° C.

WO 00/28973 describes process for the preparation of an orally administrable calcium composition, said process comprising the steps of:

obtaining a physiologically tolerable particulate calcium compound having a mean particle size in the range 3 to 40 µm, having a crystalline structure and having a surface area of 0.1 to 1.2 m2/g;

mixing said calcium compound with a water soluble diluent and an aqueous solution of a water soluble binder in a fluid bed granulation apparatus and drying the resulting mixture to produce a granulate.

US 2008/152764 describes a particulate composition comprising calcium lactate and calcium citrate microparticles having an average diameter from 0.1 µm to 20 µm, wherein the composition is in the form of particles with an average diameter from 25 µm to 1 mm, wherein the ratio by weight of calcium lactate to calcium citrate, based on the dry weight, is 80:20 to 30:70, and wherein the calcium lactate is a non-polymeric agglomeration agent for the calcium citrate microparticles. These particulate calcium lactate containing compositions exhibit good processing properties as well as good dispersion and dissolution behavior.

SUMMARY OF THE INVENTION

The inventors have unexpectedly discovered that a calcium lactate powder combining high stability with excellent water dissolution properties and a favourable taste profile can be obtained even though anhydrous calcium lactate represents the bulk of the powder if the powder additionally contains a certain amount of sodium lactate.

Thus, one aspect of the invention relates to a lactate powder having a lactate content of at least 20 wt. % and a water content of less than 3.5 wt. %, said powder comprising cationic calcium and cationic sodium, wherein said calcium and sodium are contained in the powder in a molar ratio within the range of 0.1-5.

The inventors have found that the presence of sodium lactate greatly improves the dissolution behavior of the anhydrous calcium lactate while maintaining the storage stability of the powder.

The present inventors also established that the dissolution behavior of the powder can be further improved by the addition of a fast-dissolving carbohydrate material.

The lactate powders of the invention can suitably be produced by a method comprising the steps of:

providing an aqueous liquid comprising a mixture of lactate and metal cations, said metal ions including calcium ions and sodium ions, said calcium ion and said sodium ions being present in a molar ratio that is within the range of 0.1 to 5; and drying the liquid to a water content of less than 3.5 wt. %.

The invention provides lactate powder, methods of their preparation and uses thereof, as will be explained and illustrated here below.

DETAILED DESCRIPTION OF THE INVENTION

Hence, in a first aspect, the present invention relates to a lactate powder having a lactate content of at least 20 wt. % and a water content of less than 3.5 wt. %, said powder comprising cationic calcium and cationic sodium, wherein cationic calcium and cationic sodium are present in a total amount in excess of 50% of the stoichiometric amount with regard to lactate, and wherein said calcium and sodium are contained in the powder in a molar ratio within the range of 0.1-5.

The lactate content of a material, unless indicated otherwise, refers to the amount of lactate salt that is contained in the material, including anhydrous lactate salts (e.g. calcium lactate and sodium lactate) and lactate salt hydrates (e.g. calcium lactate pentahydrate).

The term "calcium lactate" as used herein, unless indicated otherwise, refers to anhydrous calcium lactate as well as calcium lactate hydrates.

Whenever reference is made herein to the water content of a material, this includes both free and bound water. Crystal water that is contained in hydrates is an example of bound water.

The term "powder" as used herein refers to a particulate material with a volume weighted average diameter (D[4,3]) in the range of 5-2000 μm.

The term "stoichiometric quantity with regard to lactate" as used herein to quantify the calcium and sodium cations in the powder, means the amount necessary to provide counterions for all lactate ions present in the powder. Hence, an amount of 50% of the stoichiometric amount refers to an amount providing counterions for 50% of the lactate ions in the powder. As will be understood by those skilled in the art, the stoichiometric amount of lactate and monovalent sodium cations equates to a 1:1 molar ratio of lactate and sodium ions, while the stoichiometric amount of lactate and divalent calcium cations will equate to a 2:1 molar ratio. This means that a powder of the invention comprising a 2:1 mixture of calcium and sodium cations (on the basis of mol amounts) in a stoichiometric amount with regard to lactate will comprise lactate, $Ca^{2+}$ and $Na^+$ in a molar ratio of 5:2:1, as will be understood by those skilled in the art, equating to a weight ratio of approximately 22:4:1.

In a preferred embodiment of the invention, the cationic calcium and cationic sodium are present in quantities in excess of 60% of the stoichiometric amount with regard to lactate, preferably in excess of 70% of said stoichiometric amount, in excess of 80% of the said stoichiometric amount, in excess of 90% of said stoichiometric amount, in excess of 95% of said stoichiometric amount, in excess of 97% of said stoichiometric amount, in excess of 98% of said stoichiometric amount or in excess of 99% of said stoichiometric amount. In a particularly preferred embodiment, the powder of the present invention contains a stoichiometric mixture of lactate anion and metal cations, more preferably a stoichiometric mixture of lactate anion and metal cations selected from $Ca^{2+}$ and $Na^+$.

The lactate powders of the present invention, despite the fact that they contain high levels of anhydrous calcium lactate can easily be dissolved in water. Typically, the present powder has a dissolution time of less than 90 s., more preferably of less than 60 s. and most preferably of less than 30 s., when 2 g of the powder is combined with 198 ml water at ambient temperature (20° C.), ambient pressure, and under stirring. Dissolution time is determined by measuring the conductivity of the liquid. "Dissolution time" is defined as the time to reach 95% of the maximum conductivity under these conditions.

Since the total water content of the present lactate powder is less than 3.5 wt. %, the bulk of lactate salt contained in the powder is in anhydrous form. According to a particularly preferred embodiment, the water content of the lactate powder is less than 3.0 wt. %, more preferably less than 2.5 wt. %, most preferably less than 2 wt. %.

The lactate content of the present powder preferably is at least 20 wt. %, more preferably at least 30 wt. % and most preferably at least 40 wt. %.

The lactate powder typically comprises 1-20 wt. %, more preferably 2-18 wt. % and most preferably 4-16 wt. % cationic calcium, based on the total weight of the powder.

In an embodiment, the powder typically comprises 5-45 mol %, more preferably 8-40 mol %, more preferably 10-35 mol % cationic calcium, relative to lactate.

Cationic sodium is typically contained in the powder in a concentration of 1-25 wt. %, more preferably 2-20 wt. % and most preferably 2.5-16 wt. %, based on the total weight of the powder.

In an embodiment, the powder typically comprises 5-80 mol %, more preferably 10-70 mol %, more preferably 15-60 mol % cationic sodium, relative to lactate.

Lactate powders having particularly useful properties can be obtained if calcium and sodium are contained in the powder in a molar ratio that is within the range of 0.1-5, even more preferably in a molar ratio that is within the range of 0.2-4 and most preferably within the range of 0.3-3.

According to a preferred embodiment at least 50 wt. % of the alkali metal contained in lactate powder is sodium. Even more preferably at least 70 wt. %, yet more preferably at least 80 wt. % and most preferably at least 90 wt. % of the alkali metal contained in the lactate powder is sodium.

Typically, the combination of calcium lactate and sodium lactate constitutes more than 50 wt. % of the total weight of the powder. In accordance with an advantageous embodiment, the powder largely consists of calcium lactate and sodium lactate. Accordingly, it is preferred that the combination of calcium lactate and sodium lactate constitutes, more than 80 wt. % of the lactate powder, and most preferably more than 90 wt. % of the lactate powder.

Besides calcium lactate and sodium lactate, the present powder may suitably contain one or more other components. One aspect of the invention concerns the incorporation of one or more fast-dissolving carbohydrates. As noted before, the inventors established that the addition of fast-dissolving carbohydrates may further enhance the dissolution profile of the lactate containing powder. Suitable examples of fast-dissolving carbohydrates that may be used in accordance with the invention include fast-dissolving polysaccharides, fast-dissolving oligosaccharides, mono-, di- and trisaccharides, and fast-dissolving poly-alcohols. Particularly preferred saccharides are selected from the group consisting of lactose, glucose, sucrose, fructose, dextrines, dextrates and mixtures thereof. Preferred polyalcohols in accordance with the invention are selected from the group consisting of mannitol, sorbitol, xylitol, lactitol and mixtures thereof. The fast-dissolving carbohydrate employed in the lactate powder is preferably selected from lactose, sucrose, glucose, fructose, dextrines, dextrates, mannitol, sorbitol, xylitol, lactitol, and combinations thereof. Most preferably, the saccharide is glucose, lactose or mannitol.

Advantageously, the lactate powder contains 1-50 wt. %, more preferably 5-45 wt. %, more preferably 10-40 wt. %, more preferably 15-35 wt. % of the one or more fast-dissolving carbohydrates.

In case the lactate powder contains the aforementioned fast-dissolving carbohydrates, preferably calcium lactate, sodium lactate and the fast-dissolving carbohydrate together constitute more than 80 wt. % of the lactate powder, preferably more than 90 wt. % of the lactate powder The lactate powder of the present invention typically has a volume weighted mean particle size of 50-1000 µm. Even more preferably, the volume weighted mean diameter of the powder is in the range of 50-750 µm, most preferably in the range of 100-500 µm.

The aerated bulk density of the lactate powder preferably lies within the range of 350-850 kg/m$^3$. More preferably, the aerated bulk density of the powder is in the range of 400-850 kg/m$^3$, most preferably of 425-850 kg/m$^3$. The tapped bulk density of the lactate powder preferably lies within the range of 500-950 kg/m$^3$. More preferably, the tapped bulk density of the powder is in the range of 550-900 kg/m$^3$, most preferably of 575-900 kg/m$^3$.

The lactate powder according to the present invention may be produced in different manners, e.g. by drying an aqueous liquid containing the dissolved lactate salts and optional other ingredients. It is also feasible to prepare the lactate powder by dry blending the different lactate salts and other optional ingredients.

According to a particularly preferred embodiment, the lactate powder is produced by drying an aqueous liquid that contains dissolved calcium lactate and sodium lactate. Thus, the lactate powder is preferably composed of particles that contain lactate, calcium and sodium in the same relative amounts. Even more preferably, the lactate powder is composed of particles having the same composition.

According to an alternative embodiment, the present lactate powder comprises a blend of calcium lactate particles and sodium lactate particles. In accordance with one aspect of this embodiment the calcium lactate particles and the sodium lactate particles together constitute at least 80 wt. %, more preferably at least 90 wt. % of the lactate powder.

In accordance with another aspect of the latter embodiment, the lactate powder comprises a blend of calcium lactate particles, sodium lactate particles and particles of saccharide. The calcium lactate particles, the sodium lactate particles and the particles of saccharide together preferably constitute at least 80 wt. %, most preferably at least 90 wt. % of the lactate powder.

The lactate powder of the present invention preferably is composed of particles that are largely amorphous, i.e. that contain only limited amounts of crystalline material. Preferably, at least 85 wt. %, most preferably at least 90 wt. % of the lactate powder is in an amorphous state.

The lactate component of the present powder can suitably be produced by fermentation. According to a particularly preferred embodiment, the lactate powder is prepared from a culture broth containing a high level of lactate. The fermentation can typically be done using naturally selected Lactobacilli or Bacilli. For those of ordinary skill in the art it is routine practice to produce lactic acid fermentation broths that can suitably be processed into a powder of this invention. After fermentation, the broth contains primarily lactate as well as some residual components of the fermentation medium, such as carbohydrates, proteins and peptides.

In particular, besides lactate such a fermentation broth typically contains appreciable levels of fermentation components selected from, sucrose, glucose, (hydrolyzed) protein, yeast extract paste, non-lactate based salts, alkaline components such as calcium hydroxide or sodium hydroxide, biomass formed as effect of the fermentation, etc. In an embodiment, a lactate powder is thus provided containing 0.1-40 wt. %, more preferably 1-30 wt. % and most preferably 5-20 wt. % of such fermentation components.

For example, in an embodiment, the lactate powder contains, besides lactate, calcium cations and sodium cations, 10-15 wt. % lactose and/or 1-2 wt. % nitrogen and/or 0.1-5 wt. % residual biomass.

Another aspect of the invention relates to a method of producing a lactate powder as defined herein before, said method comprising the steps of:
- providing an aqueous liquid comprising a stoichiometric mixture of lactate and metal cations, said metal ions including calcium ions and sodium ions, said calcium ions and said sodium ions being present in a molar ratio that is within the range of 0.1-5; and
- drying the aqueous liquid to a water content of less than 3.5 wt. %.

The lactate powder may suitably be formed during the drying step, e.g. by breaking up the aqueous liquid into small droplets and removing the water from these droplets, e.g. by spray drying. Alternatively a solution is sprayed on an agitated bed to form particles of the desired composition. A drying step is usually included in such a process. Alternatively, the powder may be produced by first drying the aqueous liquid to produce a dry residue (e.g. by means of drum drying) and optionally by subsequently reducing the size of the dry residue by, for instance, grinding, milling or cutting. Alternatively, a blend of the materials with the desired composition is produced starting with pure ingredients.

Preferably drying of the aqueous liquid comprises spray drying of the aqueous liquid. In the present method, prior to the spray drying, aqueous liquid may be concentrated by evaporation. Preferably, the aqueous liquid has a dry matter content of 1-80 wt. %, most preferably of 10-60 wt. % when it is fed into a spray dryer.

As explained herein before, it can be advantageous to incorporate saccharide in the lactate powder of the present invention. Accordingly, in a preferred embodiment, the aqueous liquid further comprises a saccharide or poly alcohol, said saccharide being selected from the group consisting of lactose, glucose, sucrose, fructose, dextrines or dextrates and combinations thereof. Most preferably, the saccharide is glucose or lactose. The polyalcohol is preferably selected from mannitol, sorbitol, xylitol, lactitol, and mixtures thereof.

According to a particularly preferred embodiment, the aqueous liquid employed in the present method is a fermentation broth, notably a fermentation broth that is obtained by fermenting a suitable medium with a micro-organism selected from Lactobacilli or Bacilli.

Yet another aspect of the present invention relates to a process of producing a product selected from a foodstuff, a beverage, a pharmaceutical product and a nutritional formulation, said process comprising the dissolution of a lactate powder as defined herein before in an aqueous liquid phase and incorporating said aqueous liquid phase in the product.

The aforementioned process typically comprises combining the lactate powder with one or more other edible or potable ingredients other than water. Preferably, lactate powder is combined with the one or more other edible or potable ingredients in an amount of 0.1-5.% by weight of the product.

The invention is further illustrated by the following non-limiting examples.

EXAMPLES

Example 1

Anhydrous Calcium lactate was produced by exposing calcium lactate pentahydrate to a 100° C. environment with dry air for a period of around 3 hrs. The moisture content of this product was 1.1% proving that the material is essentially free of water and amorphous. Solid sodium lactate was used as such as solid material. Mannitol and glucose were used as such. Lactose was made amorphous by freeze drying a solution of lactose in water.

For dissolution test mixtures of total weight of 2 gram were produced. Starting materials were accurately weighed in a plastic cup and two glass beads with a diameter of 6 mm were added. The blend was manually mixed for 1 min. To prevent water uptake, the air was purged with dry nitrogen.

Dissolution tests were performed by adding the test sample to 198 gram demineralized water which was stirred with a stirring flea. The test conditions are such that sink conditions are always fulfilled (i.e. after complete dissolution of the material concentration in the liquid is less than around 30% of saturation solubility. Times to reach 10%, 50%, 90% and 95% (t(10), t(50), t(50) and t(95), respectively) of complete dissolution were calculated.

TABLE 1 sample compositions (in mass %) and dissolution characteristic values (in seconds)

| Test No. | $CaL_2$ | NaL | Lactose | Mannitol | Glucose | t(10) | t(50) | t(90) | t(95) |
|---|---|---|---|---|---|---|---|---|---|
| 1 | 100 | 0 | 0 | 0 | 0 | 1 | 6 | 40 | 127 |
| 2 | 95 | 5 | 0 | 0 | 0 | 1 | 7 | 53 | 195 |
| 3 | 80 | 20 | 0 | 0 | 0 | 1 | 6 | 16 | 23 |
| 4 | 60 | 40 | 0 | 0 | 0 | 1 | 5 | 13 | 21 |
| 5 | 40 | 60 | 0 | 0 | 0 | 1 | 7 | 20 | 25 |
| 6 | 20 | 80 | 0 | 0 | 0 | 1 | 8 | 19 | 22 |
| 7 | 0 | 100 | 0 | 0 | 0 | 2 | 9 | 18 | 21 |
| 8 | 64 | 16 | 20 | 0 | 0 | 1 | 7 | 15 | 18 |
| 9 | 56 | 14 | 30 | 0 | 0 | 1 | 5 | 14 | 19 |
| 10 | 48 | 12 | 40 | 0 | 0 | 1 | 5 | 16 | 21 |
| 11 | 64 | 16 | 0 | 20 | 0 | 2 | 8 | 16 | 20 |
| 12 | 48 | 12 | 0 | 40 | 0 | 1 | 7 | 15 | 19 |
| 13 | 64 | 16 | 0 | 0 | 20 | 1 | 6 | 14 | 18 |
| 14 | 48 | 12 | 0 | 0 | 40 | 1 | 5 | 5 | 9 |
| 15 | 76 | 4 | 20 | 0 | 0 | 1 | 6 | 13 | 16 |
| 16 | 66.5 | 3.5 | 30 | 0 | 0 | 1 | 5 | 12 | 14 |
| 17 | 57 | 3 | 40 | 0 | 0 | 1 | 5 | 12 | 14 |

Example 2

Different blends of Calcium lactate pentahydrate or calcium lactate anhydrate and sodium lactate have been produced using a tumbling mixer. The samples have been stored in hermetically sealed glass jars to prevent any moisture exchange. The samples have been stored at temperatures of 4° C., room temperature (around 18-22° C.) and 40° C. The properties of the powders have visually been assessed at different time-points. The figure illustrates that blend containing calcium lactate anhydrate and sodium lactate stays a free-flowing powder. The blend containing calcium lactate pentahydrate and sodium lactate form a cake. All samples containing calcium lactate anhydrate and sodium lactate were free flowing powders, the table summarizes the visual observations of the blends containing calcium lactate pentahydrate

TABLE 2

Summary of visible observations of Calcium lactate pentahydrate ($CaL2·5H2O$) - sodium lactate (NaL) blends

| NaL (%) | $CaL_2·5H_2O$ (%) | T (° C.) | T = 0 days | T = 30 days |
|---|---|---|---|---|
| 20 | 80 | 4 | Flowable powder | no visible changes |
| | | RT | Flowable powder | slight moist spots, one powder block |
| | | 40 | Flowable powder | liquid areas visible on surface, wet lumps |
| 40 | 60 | 4 | Flowable powder | no visible changes |
| | | RT | Flowable powder | one powder block |
| | | 40 | Flowable powder | one powder block, wet spots on top |
| 60 | 40 | 4 | Flowable powder | very weak lumps when shaked |
| | | RT | Flowable powder | one powder block |
| | | 40 | Flowable powder | more liquid spots, one powder block |
| 80 | 20 | 4 | Flowable powder | very weak lumps when shaked |
| | | RT | Flowable powder | one powder block |
| | | 40 | Flowable powder | saturated spots, one powder block |

To quantify the degree of cake formation, a mixture containing 20% sodium lactate and 80% calcium lactate pentahydrate has been stored at a temperature of 40° C. for a period of 5 days in a cylinder used for the purpose of testing the unconfined fracture strength of cylindrical specimen. After storage for 5 days at a temperature of 40° C., a cake with a fracture strength of 8 kPa was formed when calcium lactate pentahydrate was present. The material was still flowing meaning that the unconfined fracture strength could not be measured when a mix based on anhydrous calcium lactate was tested.

Example 3

Calcium lactate pentahydrate was placed in a fluidized bed equipped with a top spray system. The (set point) inlet air temperature was 100° C. during fluidization. Sodium lactate solution containing 60% sodium lactate was sprayed on fluidized calcium lactate to form particles in a calcium lactate to sodium lactate ratio of 1:1 and 4:1 respectively. Dissolution time was detected according to the method in Example 1. Table 3 shows the dissolution results.

TABLE 3 sample compositions (in mass %) and dissolution characteristic values (in seconds)

| Test No. | $CaL_2$ | NaL | t(10) | t(50) | t(90) | t(95) |
|---|---|---|---|---|---|---|
| 18 | 50 | 50 | 1 | 3 | 6 | 10 |
| 19 | 80 | 20 | 1 | 9 | 29 | 77 |

Example 4

A lactic acid ferment was produced having (relative) amounts of lactate and calcium and sodium cations according to this invention. The raw ferment was not purified and processed into a powder having the composition indicated in table 4 by spray-drying. The product temperature during the spray-drying process was 90° C., the air temperature varied between 165 and 180° C.

Dissolution time has been determined according to the methodology described in example 1. The average dissolution time of this raw ferment was 32 s.

TABLE 4

Composition of raw ferment

| Component | Content (% by weight) |
| --- | --- |
| Lactate | 50.6 |
| Sugars | 10.8 |
| Calcium | 7.7 |
| Sodium | 2.9 |
| Raw protein | 9.4 |
| Moisture | 3.2 |

The invention claimed is:

1. A lactate powder, comprising at least 80 wt. %, based on the total weight of the lactate powder, of a mixture of calcium lactate salt and sodium lactate salt and having less than 3.5 wt. % of water, wherein the powder comprises 10-45 mol % cationic calcium relative to lactate and 15-80 mol % cationic sodium relative to lactate, wherein at least 50 wt. % of the metal cations contained in the powder is sodium, and wherein the lactate powder has been produced by spraying a solution of sodium lactate on an agitated bed of particles of calcium lactate.

2. The lactate powder according to claim 1, having a dissolution time of less than 30 seconds, when 2 g of the powder is dissolved in 198 ml water under ambient pressure and temperature and while stirring.

3. The lactate powder composition according to claim 1, wherein at least 70 wt. % of the metal cations contained in the powder is sodium.

4. The lactate powder composition according to claim 3, wherein at least 80 wt. % of the metal cations contained in the powder is sodium.

5. The lactate powder according to claim 1, wherein the combination of calcium lactate and sodium lactate constitutes more than 90 wt. % of the lactate powder.

6. The lactate powder according to claim 1, further comprising 1-50 wt. % of a carbohydrate.

7. The lactate powder according to claim 6, wherein the carbohydrate is selected from the group consisting of lactose, sucrose, glucose, fructose, dextrines, dextrates, mannitol, sorbitol, xylitol, lactitol, and combinations thereof.

8. The lactate powder according to claim 1, having a volume weighted mean particles size (D[4,3]) in the range of 5-2000 μm.

9. The lactate powder according to claim 1, wherein the lactate powder comprises particles having the same composition.

10. The lactate powder according to claim 1, wherein at least 85 wt. % of the lactate powder is in an amorphous state.

11. The lactate powder according to claim 1, wherein calcium and sodium are contained in the powder in a molar ratio of at least 0.1.

12. The lactate powder according to claim 1, wherein the powder has a water content of less than 2 wt. %.

13. A process of producing a product selected from a foodstuff, a beverage, a pharmaceutical product and a nutritional formulation, the process comprising dissolving a lactate powder according to claim 1 in an aqueous liquid phase and incorporating the aqueous liquid phase in the product.

* * * * *